United States Patent [19]
Collins et al.

[11] Patent Number: 5,318,754
[45] Date of Patent: Jun. 7, 1994

[54] MICROWAVE ASHING APPARATUSES AND COMPONENTS

[75] Inventors: Michael J. Collins, Charlotte; Wyatt P. Hargett, Matthews, both of N.C.

[73] Assignee: CEM Corporation, Matthews, N.C.

[21] Appl. No.: 5,252

[22] Filed: Jan. 15, 1993

Related U.S. Application Data

[60] Continuation of Ser. No. 298,554, Jan. 18, 1989, abandoned, which is a continuation-in-part of Ser. No. 811,539, Dec. 19, 1985, abandoned, which is a division of Ser. No. 487,307, Apr. 21, 1983, Pat. No. 4,565,669.

[51] Int. Cl.[5] ............................................. G01N 31/12
[52] U.S. Cl. .................................... 422/109; 422/288; 422/300; 422/307; 219/757; 219/710
[58] Field of Search .................... 73/864.91; 220/4.21, 220/200; 219/10.55 R, 10.55 A, 10.55 D, 10.55 E, 10.55 F, 10.55 M; 422/78, 82.12, 102, 104, 109, 198, 288, 300, 307; 436/155, 160

[56] References Cited

U.S. PATENT DOCUMENTS

| | | | |
|---|---|---|---|
| 4,080,168 | 3/1978 | Abu-Samra et al. | 422/101 X |
| 4,307,277 | 12/1981 | Maeda et al. | 219/10.55 R |
| 4,347,216 | 8/1982 | Kawasaki et al. | 422/78 |
| 4,547,643 | 10/1985 | Yamauchi | 219/10.55 R |
| 4,565,669 | 1/1986 | Collins et al. | 422/78 |
| 4,568,426 | 2/1986 | Orlando | 422/78 X |
| 4,814,300 | 3/1989 | Helferich | 428/318.8 X |
| 4,861,556 | 8/1989 | Neas et al. | 422/78 |
| 4,882,286 | 11/1989 | Neas et al. | 436/175 |
| 5,066,843 | 11/1991 | Revesz | 219/10.55 R |

OTHER PUBLICATIONS

Emerson & Cuming, Technical Bulletin 6.2.12A, "Eccofoam Q" Revised Apr. 1977, 1 page.
Whatman, "Technical Data on Ultra-Pure QM-A Quartz Filters" Publication No. 860 QM-AA, 2 pages.
CEM Corporation, "Microwave Drying/Digestion System MDS-81" 1981, 4 pages.

Primary Examiner—James C. Housel
Assistant Examiner—Jeffrey R. Snay
Attorney, Agent, or Firm—Raymond F. Kramer

[57] ABSTRACT

An apparatus for use in analyzing materials for ash content includes a walled chamber which retains microwave radiation therein, a source of microwave radiation, such as a magnetron, for radiating onto contents of such chamber, and an ashing furnace in the chamber which includes a heat resistant wall of low thermal conductivity, which is transmissive of microwave radiation, and a microwave absorptive material which is capable of being heated by microwave radiation to an ashing temperature. The furnace includes a passageway through it for the entry into the furnace cavity of a gas, such as air, and for venting gas, such as combustion products, from the furnace cavity, and preferably also includes a removable trapezoidally shaped door in a front wall thereof, which, when the chamber door is open, is readily removable from the furnace by hand, without burning the operator's fingers, despite the high internal temperature in the furnace cavity. Air flows through the chamber and around the furnace, helping to cool the exterior, of the furnace walls. It is preferred that the operation of the furnace and the ashing temperature be controlled by a combination of a temperature sensor, preferably a thermocouple, and a control mechanism, which turns the magnetron on and off as the temperature in the furnace cavity falls below or rises above a desired set temperature, respectively.

17 Claims, 6 Drawing Sheets

MICROWAVE ASHING APPARATUSES AND COMPONENTS

This application is a continuation of Ser. No. 07/298,554, filed Jan. 18, 1989, now abandoned, which is a continuation-in-part of Ser. No. 06/811,539, filed Dec. 19, 1985, now abandoned, which is a division of Ser. No. 06/487,307, filed Apr. 21, 1983, which issued as U.S. Pat. No. 4,565,669. The disclosure of such applications and patent are incorporated herein, by reference.

The present invention relates to microwave ashing and analytical apparatuses, components of such apparatuses, and processes. More particularly, the present invention relates to such apparatuses which include a source of microwave radiation, a walled chamber into which microwave radiation is directed, which chamber retains such radiation therein, and an ashing furnace in the chamber, the walls of which furnace are heat resistant, of low thermal conductivity, and transmissive of microwave radiation. The furnace also includes a microwave absorptive material which is capable of being heated to an ashing temperature, temperature sensing means, useful to regulate the temperature in the furnace cavity, passageways for gas through the furnace cavity and through the walled chamber, and a removable door in the front side wall of the furnace. Although other heat resistant holders for the ashable samples may be used in the furnace it is preferred that such a holder be a container which is light in weight, microwave transmissive and porous, and of such containers those of quartz microfibers are highly preferred. The invention also relates to various components of the described apparatus and to uses of the apparatus in ashing and analytical procedures.

In the previously mentioned U.S. patent applications and patent there are described apparatuses and processes for ashing an ashable material by heating an ashing means, such as silicon carbide, by means of microwave radiation, and ashing a sample to be analyzed, which may be resting on a support made of fused quartz fibers, by means of the heat generated in the ashing means. In such apparatuses the silicon carbide rests on a refractory material and the sample to be ashed is placed on a relatively thin quartz pad which is in contact with the silicon carbide. Such apparatus is positioned inside a computer controlled analytical apparatus, such as the MDS-81 microwave drying/digesting system, manufactured by CEM Corporation, which is described in their bulletin entitled *CEM Corporation Microwave Drying-/Digestion System MDS-81 (laboratory microwave system)*, published in 1981, which is hereby incorporated herein by reference.

Although the microwave ashing apparatus and process of the mentioned application and patent are useful in speeding ashing operations and analytical determinations dependent on them, the present inventors continued their efforts to improve microwave ashing and analyses for ash content, and such experimentation has led to the present invention. In the invented apparatuses and processes the sample to be ashed is in a furnace made of microwave transmissive (preferably essentially or completely microwave transparent material), which is an open celled ceramic foam, preferably an open celled fused quartz foam. Such furnace material and the furnace structure help to maintain the ashing temperature uniform throughout the furnace cavity and additionally, such temperature is maintained at a desired level by a thermocouple control system, the probe of which is in the furnace cavity. More uniform heating of the ashable sample makes the ashing operation more consistent and more accurate. Furthermore, possible loss of sample material in air leaving the microwave apparatus is minimized and it has been found that it is usually unnecessary to employ a cover sheet of fused quartz fiber pad material to hold the ash in place and to prevent it from being carried off in the exhaust air. Thus, the tare weight may be less when using the invention and therefore weighings can be more accurate. Various other advantages attend the present invention, including ease of use of the apparatus, ready removability and replaceability of the furnace door, improved burning off of solvent from the ashable sample, which solvent accompanies any magnesium acetate ashing aid employed, accurate automatic control of ashing conditions, and quicker ashings.

Although various ashing apparatuses for analytical purposes have been described in detail in the literature, most of them utilize muffle furnaces to generate heat and they employ crucibles to hold the samples to be ashed. So far as applicants know, before the filing of their U.S. Pat. No. 4,565,669, no other microwave ashing apparatus and process had been described in the literature. In U.S. Pat. No. 4,307,277 a microwave heating oven was disclosed for heating materials to high temperatures, as in producing a sintered ceramic. However, the heating ovens of that patent were not thermostatically controlled, did not employ applicants' open celled ceramic material for furnace walls and door, and were different from applicants' apparatus in various other important structural features. The various changes incorporated into the present invention are improvements over the structures and processes of U.S. Pat. Nos. 4,307,277 and 4,565,669 and contribute to the improved analytical results and quicker ashings that are obtained when employing the present invention.

In accordance with this invention an apparatus for ashing ashable samples comprises a walled microwave retaining chamber, a source of microwave radiation for radiating onto contents of such chamber and an ashing furnace within the chamber having a furnace wall of heat resistant material about an internal furnace cavity, with an opening in said wall for insertion and removal of an ashable sample, a door of heat resistant material for closing and opening the opening in the furnace wall, a microwave absorptive material which is capable of being heated to an ashing temperature by microwave radiation, and a passageway through the furnace for passing gas into the furnace cavity and for venting gas from said cavity, which heat resistant furnace wall and furnace door material is of low thermal conductivity and is essentially transparent to microwave radiation, which microwave absorptive material of the furnace has a surface thereof exposed to the furnace cavity, and which microwave retaining chamber wall has inlet and outlet openings therein for the passage of gas into and out of the chamber, around the furnace. In preferred embodiments of the invention a thermocouple or other suitable temperature sensing means is employed in controlling the temperature in the furnace cavity, air is controllably passed through the furnace and through the walled microwave retaining chamber, a microwave transmissive door with a handle or gripping means on it is used to close a doorway opening in the furnace, silicon carbide is the microwave absorptive material employed and is present as strips and/or slabs in the furnace wall interior, the material of construction of the furnace is a microwave transparent open celled quartz material, and a container which is employed to hold the ashable sample is a heat resistant light weight, porous, walled container of essentially microwave transparent quartz microfibers which allow gas flow therethrough but prevent passage of ash. Also within the invention are components of the described apparatus, such as the furnace, with a removable and adjustable door, and a process for ashing and analyzing an ashable material.

BRIEF DESCRIPTION OF THE DRAWINGS

The invention will be readily understood by reference to this specification, including the accompanying drawing, in which:

In FIG. 1 ashing apparatus 11 includes a walled microwave retaining chamber like that of a CEM MDS-81 Microwave Drying/Digestion System, which is defined by a bottom, two sides, a top, a rear, a front, and a door, which chamber wall is represented by numeral 13, shown applied to a side wall of the chamber. Door 15 is shown in open position so that ashing furnace 17 may be seen. Such ashing furnace will be described in greater detail subsequently in the description of FIG. 3. Temperature controller 19 is connected to a thermocouple probe 21 in the furnace cavity by an electrical connector, not illustrated. The flow of air into the chamber, into the furnace cavity and out of the cavity and chamber will be described with reference to FIG. 2, as will be the operating and display panels of the "microwave system" portion of the apparatus, which panels are like those of the CEM Corporation Microwave Drying-/Digestion System (MDS-81).

In FIG. 2 air (or gas) flow through the ashing apparatus is represented by the dotted arrows. Air enters the walled microwave retaining chamber, designated by numeral 23, through grill openings 25 and 27 in chamber side walls 29 and 31, which openings are located near the bottom of the chamber, and passes upwardly and around furnace 17, cooling the exterior thereof, after which it passes out through suction opening or duct 33, from whence it is discharged from the apparatus through an air exhaust duct, as illustrated in FIG. 5, preferably to a fume hood or in other permissible manner. In FIG. 2, furnace door 35, which is substantially trapezoidal in horizontal cross-section, with handle portions or finger grips cut into the base of the trapezoid (the front of the door), is in place in the furnace wall but the door opening is not completely closed, thereby allowing passage of air into the furnace cavity (not shown in FIG. 2), as represented by arrows 37 and 39. Although the arrows indicate the air flow under the door, air also enters the furnace cavity through the side clearances between the door and the furnace wall. Similarly, air may leave the furnace cavity through the top thereof, as represented by arrows 41 and 43, and the upper portions of the side openings. Arrow 45 represents the passage of air and combustion products out of the furnace cavity through vertical bore 47 (actually such passage is through the clearance between the wall of said bore in the upper part of the furnace 17 and thermocouple probe 21). The gas exhausted from the furnace cavity passes out through exhaust duct 33 to a suitable hood or other discharge means. Thus, there are created passageways for the air or other gas through the furnace, and through the chamber and furnace cavity. It should be mentioned that air inlet openings 25 and 27 and exhaust duct opening 33 are shielded by shielding material (not specifically shown) to prevent escape of microwave radiation from the microwave retaining chamber. The chamber walls and door are of a metal or metal alloy, such as aluminum or stainless steel, and may be coated with a radiation transmissive polymer, such as polytetrafluoroethylene. Alternatively, but not as desirably, the door may be glass lined and shielded to prevent any escape of radiation.

Figure 2:
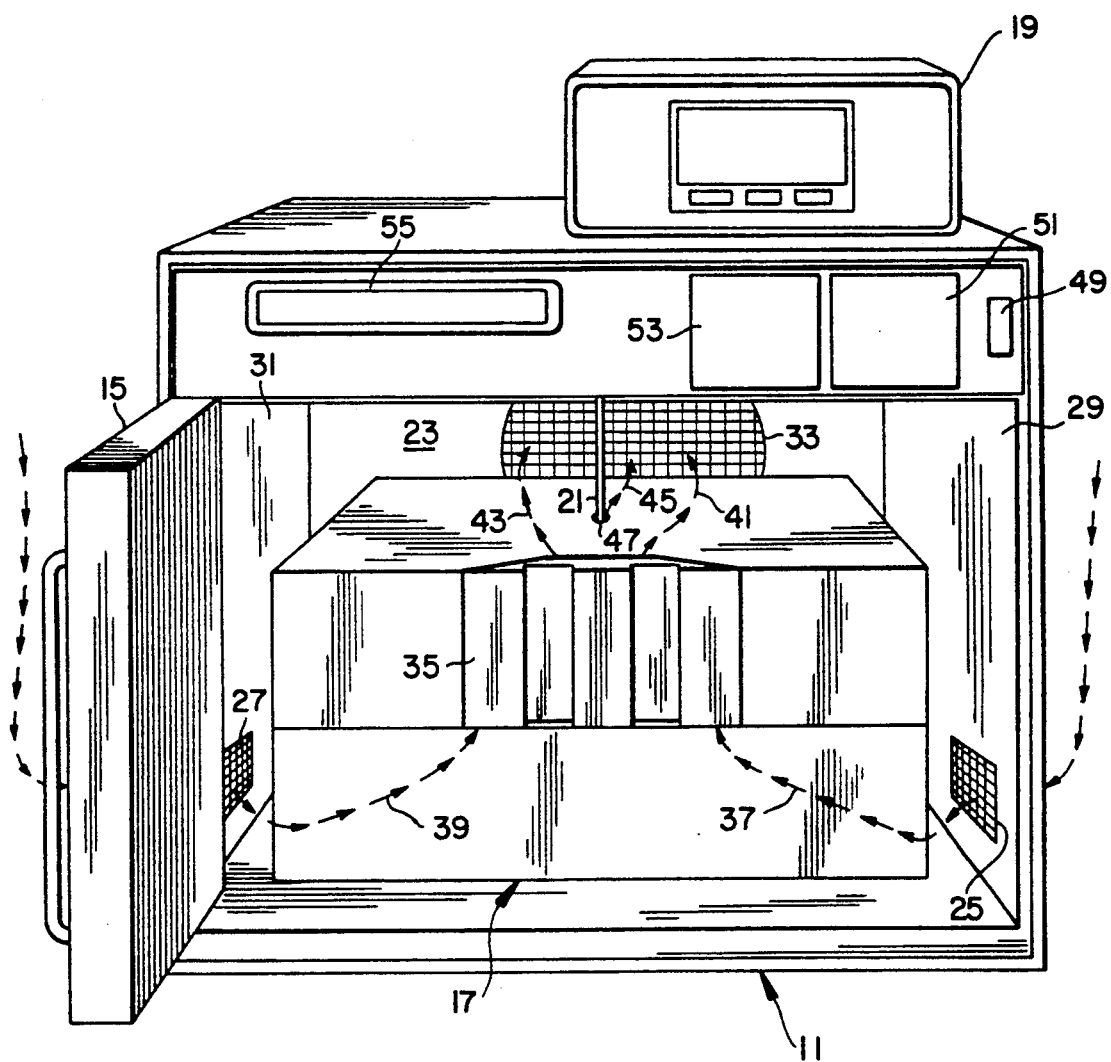
FIG. 2 is an enlarged front perspective view like that of FIG. 1, with the furnace door in place, in almost closed position, with arrows indicating air flow into the chamber, into the furnace, out of the furnace and out of the chamber.

The temperature controller 19 includes three control keys and a display. The keys are marked S, increase and decrease (not so marked in FIG. 2), and the use thereof will be mentioned later in connection with a description of how the controller is programmed. The "microwave system" portion of the apparatus includes controls like those of the CEM MDS-81 laboratory microwave system. Such are an on-off switch 49, and control panels 51 and 53. Panel 51 includes Program, Reset, Enter, Stop and Start keys and panel 53 includes numerals 1, 2, 3, 4, 5, 6, 7, 8, 9, and 0 (none of which is specifically illustrated). Display 55 is of alphanumeric type.

Figure 3:
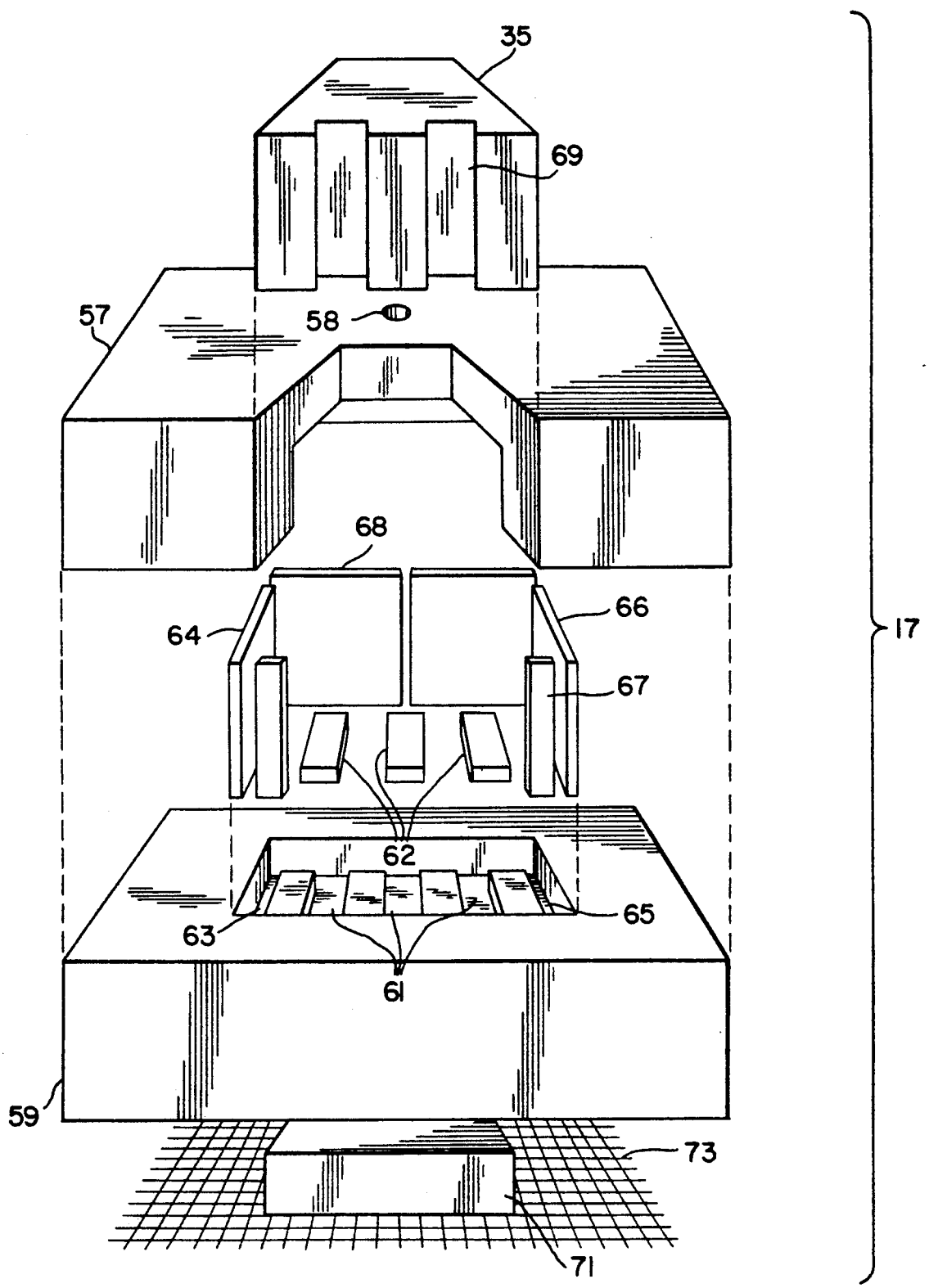
FIG. 3 is an enlarged disassembled view of the ashing furnace assembly, with a base support and a protective screen under such support.

The ashing furnace 17, illustrated in FIG. 3, includes combinable and separable unitary upper and lower sections. Upper portion 57 is of a material of heat resistant and microwave transmissive properties, which is also of low thermal conductivity, preferably being an open celled fused quartz foam. A vertical bore or hole 58 allows passage through such upper portion of a thermocouple probe and connector, (neither being shown in this view). Ashing furnace 17 also includes a unitary separable lower portion 59 of the same heat resistant material, which contains a cavity therein which, together with a mating cavity in the upper furnace portion, forms the furnace cavity. Lower portion 59 includes a plurality of slots or grooves 61 at the bottom thereof and other slots or grooves, such as those illustrated at 63 and 65. Grooves 61 are for positioning floor heating elements 62 and grooves 63 and 65 are for positioning the heating elements 64 and 66, respectively. Similar grooves, not visible in FIG. 3, are provided for positioning front heating elements 67 and back heating elements 68. Ceiling heating elements (not shown) may also be provided in upper portion 57 of the furnace, in suitable slots, grooves, channels or other holding means therein. The various heating elements are of microwave absorptive material that is capable of being heated to an ashing temperature by microwave radiation. A much preferred such material is silicon carbide, and preferably the heating elements are separated, with surfaces that are flush with the furnace cavity interior walls. Furnace door 35, which is shown as being of trapezoidal horizontal cross-section (but may be of other suitable cross-section) matches in shape a corresponding wall opening in the front of the upper furnace portion, and when it is in place its interior and the upper and lower wall portion interiors define the furnace cavity. The door includes in the front face thereof a pair of grooves 69 which function as parts of a handle or gripping means to permit easy hand removal, closure or adjustment of the door position. The furnace is supported by a refractory block 71 which is under a minor proportion of the furnace bottom surface. Such support allows circulation of air or other gas under much of the furnace bottom, thereby facilitating cooling of it. Under the refractory support there is shown a separator, such as a cloth or screen, which may be of temperature resistant plastic, metal or other suitable material. The function of the cloth or screen is to prevent scratching of the finish of the chamber interior by the refractory support, which often has rough surfaces.

Figure 1:
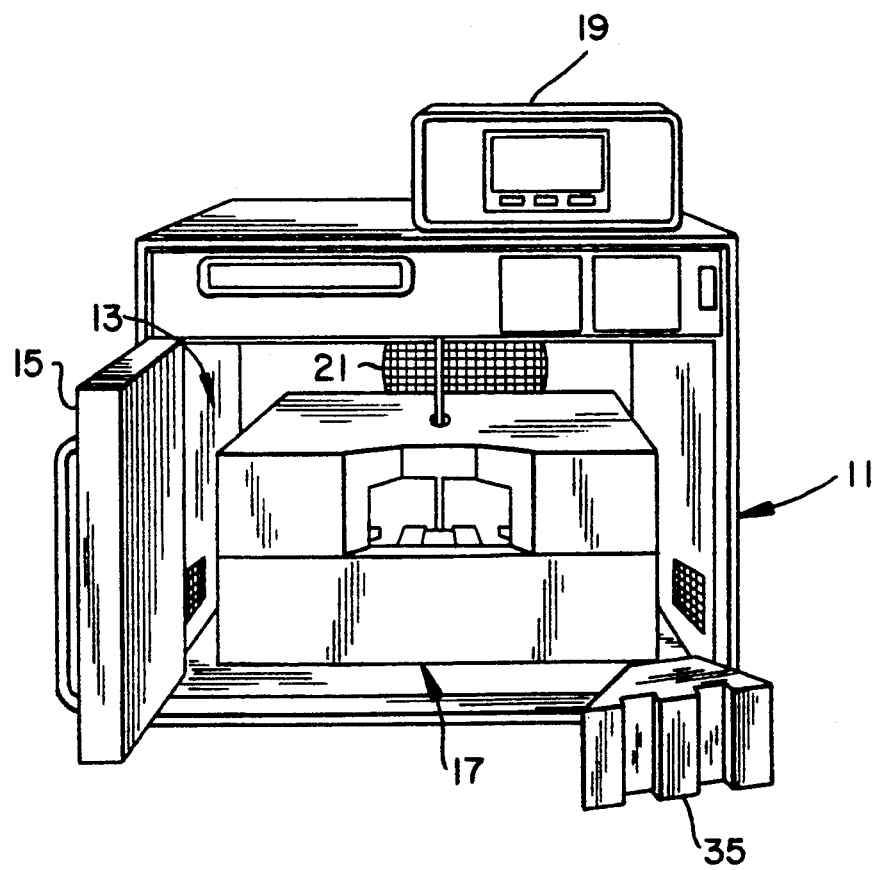
FIG. 1 is a front perspective view of the microwave ashing apparatus of this invention, with the chamber door open, with the furnace door removed and without any ashable sample in the furnace.
Figure 4:
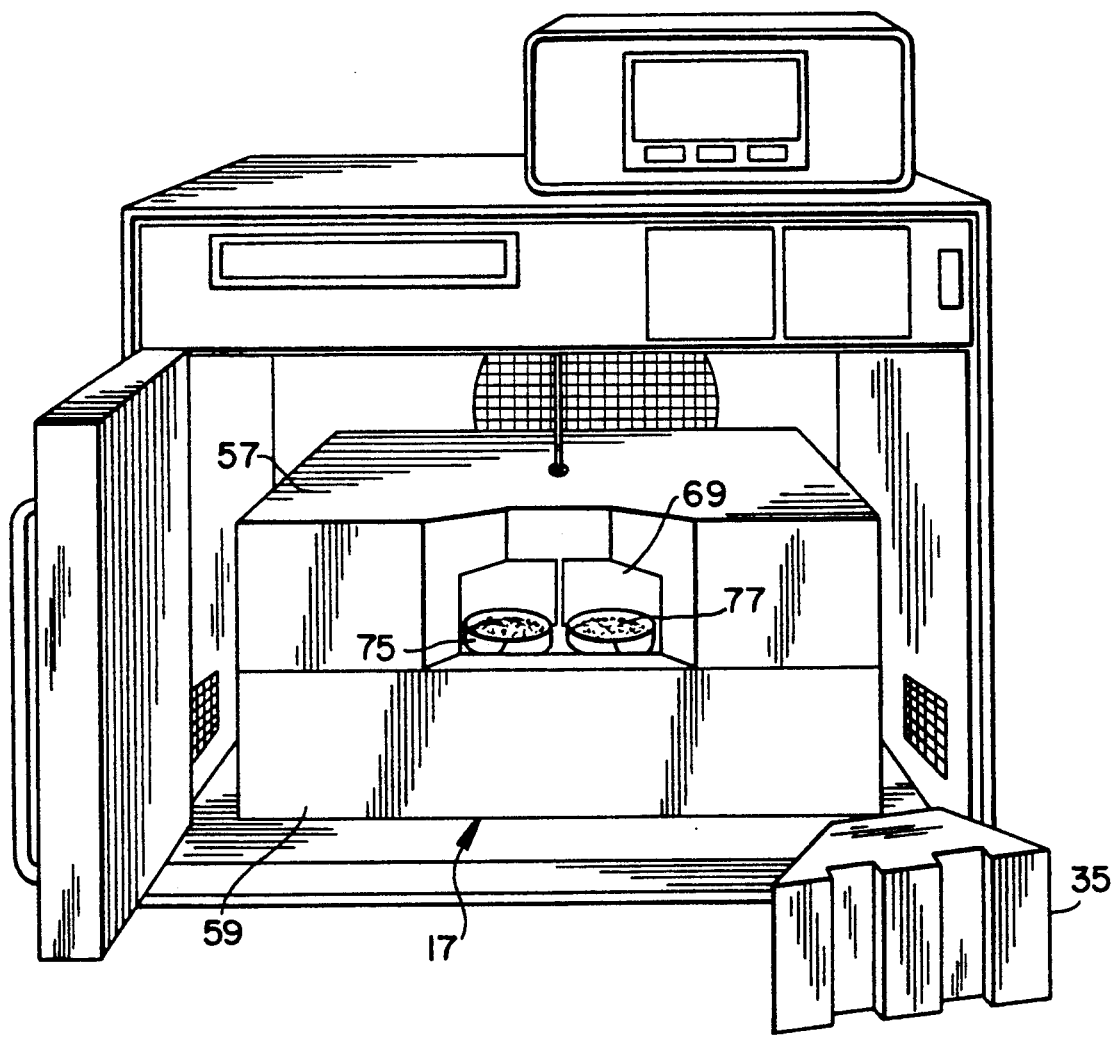
FIG. 4 is a front perspective view corresponding to that of FIG. 1 but illustrating two containers of ashable material in the furnace.

Because FIG. 4 is essentially the same as FIG. 1 except for the presence in the furnace cavity of FIG. 4 of a pair of containers of ashable material (or ash), only that aspect of FIG. 4 will be described further herein. In FIG. 4 ashing furnace 17 is comprised of separable upper and lower portions 57 and 59, respectively, together with the heating elements illustrated in FIG. 3, of which rear heating elements 69 are visible in FIG. 4, and such parts define the ashing cavity when door 35 is in place. In such cavity are positioned two porous, walled containers 75 of quartz microfiber sheet material. In the containers are suitable charges of material 77 to be ashed (or they may contain the resulting ash). Details of the ashing procedure will be described later in this specification.

Figure 5:
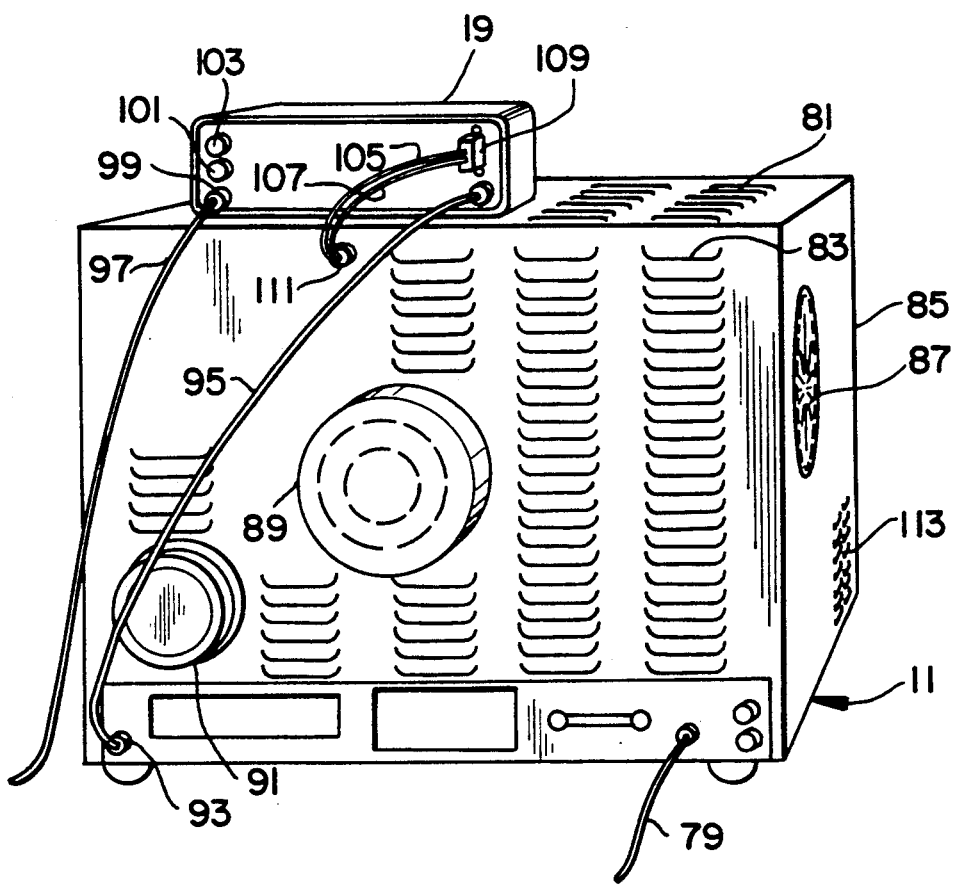
FIG. 5 is a rear perspective view of the exterior of the microwave ashing apparatus with a temperature control unit in place thereon.

In FIG. 5 ashing apparatus 11 is illustrated with temperature controller 19 in position thereon, with a thermocouple (in the furnace cavity) connected to the controller. Numeral 79 identifies the power cord to the ashing apparatus and louvers 81 and 83 are to permit airflow through an air jacket around the chamber to help cool the chamber exterior. Between the outer wall 85 and the chamber there is located a magnetron from which microwave radiation is directed into the radiation retaining chamber, the walls of which are of microwave reflective material, such as stainless steel or other suitable metal or alloy, which may be coated with a paint or polymeric protective coating. The magnetron is a standard part in microwave apparatuses of the present type and is concealed within walls thereof. Therefore, it is not illustrated in the present drawing. Neither is there shown any cooling fan for the magnetron, although such a fan is present in the apparatus. Numeral 87 indicates an opening in the apparatus for exhausting the air that is blown across the magnetron to cool it. A blower (not illustrated) is provided within the apparatus to exhaust air and combustion gases from the furnace and to create an air flow through the chamber and through the furnace. The motor for such blower is designated by numeral 89 and the corresponding exhaust is identified by numeral 91. Openings 113 correspond to air inlets 25 and 27 (in FIG. 2) and are for admission of air to the apparatus chamber (and furnace cavity). A receptacle 93 is provided for connection of the temperature controller cable 95. Electric power cord 97 is connected to controller 19 at 99. A fuse is provided at 101 and a power switch is indicated at 103.

Thermocouple connector leads 105 and 107 are connected to a thermocouple connector plug 109 and such leads or connector are/is also connected to a thermocouple (not illustrated in FIG. 5), which is preferably located in the top central portion of the furnace cavity. Such connector enters the ashing apparatus 11 at 111.

Figure 6:
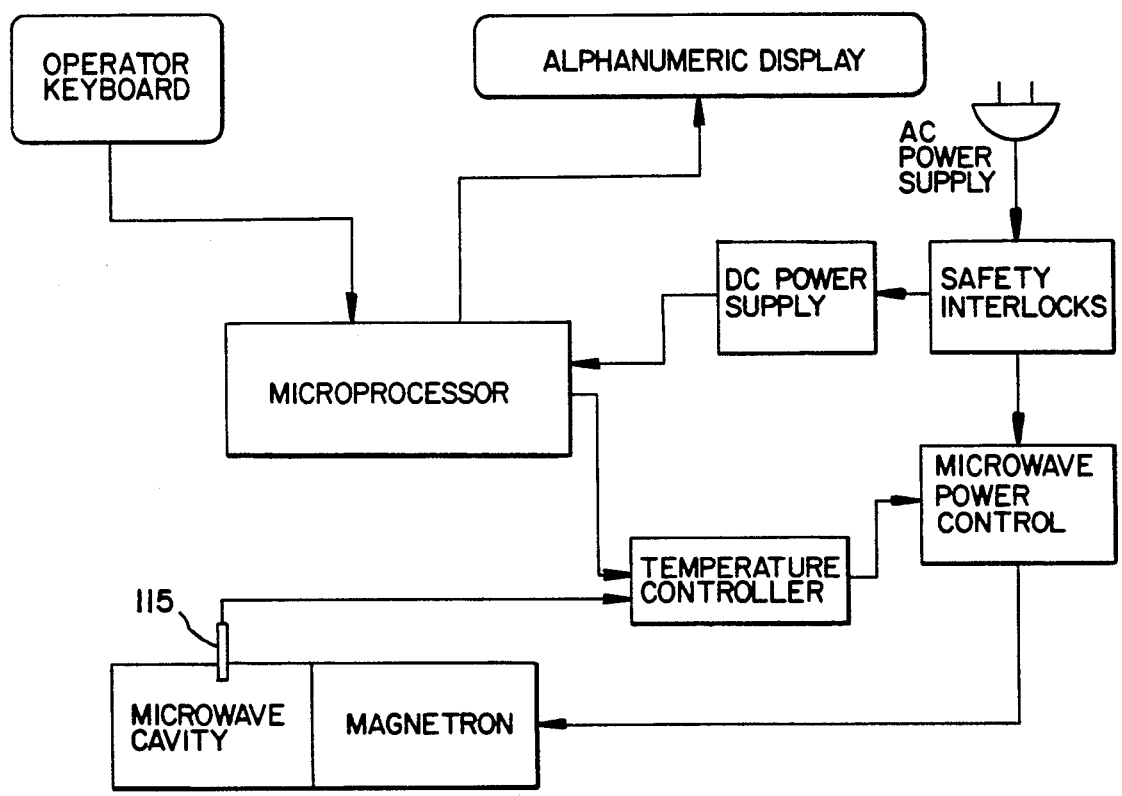
FIG. 6 is a schematic electrical circuit diagram of various elements of the microwave ashing apparatus.

In FIG. 6 the relationship between the operator keyboard (and alphanumeric display), the microwave processor, the temperature controller, the thermocouple and the power control to the magnetron is illustrated. The operator keyboard controls the amount of power employed and the time of heating, which are displayed in the alphanumeric display after they are set by keyboard operation. The temperature controller controls the ashing temperature and permissible variation of the temperature (often $\pm 2°$ or $\pm 3°$ C.) from that which is set. Thermocouple 115 inputs the temperature controller with the temperature in the furnace cavity and the controller operates the microwave power control to switch the magnetron off when the temperature is higher than set and switches the magnetron back on when the temperature falls below the set point. More details about the operation of the apparatus operator keyboard and temperature control will be given subsequently.

The apparatus for the application of enough microwave energy so a sample of material can be ashed may be any such suitable microwave apparatus that can direct microwave radiation onto the heating elements in the furnace. As was indicated previously, a CEM Corporation MDS-81 system is useful but similar systems can also be employed, together with an internal furnace, temperature control and container for the ashable material. Preferably the system will incorporate a microprocessor, a digital computer and controls for regulating the application of microwave radiation to the elements to be heated. Thus, the microwave radiation may be applied for desired lengths of time and at different levels of radiation, if desired, but often the radiation level will be constant at the maximum design capacity. Key elements of the microwave system utilized will be proper gas (air) flow through it for cooling of the furnace, and no microwave load in the system except that in the furnace. Also, the furnace should be such as to allow exhaustion of combustion gases and inflow of fresh gas (air or suitable oxidizer).

It is noted that in some of the apparatuses referred to the microwave power range may be from 1 to 100% of full power (500 to 1,500 watts in some instances) in 1% increments. Of course, lesser and greater powers may also be employed, for example up to several kilowatts, e.g., 0.3 to 5 or 0.4 to 2 kw., but 0.9 or 1 kw. will usually suffice. In the United States the frequency of microwave radiation employed will normally be 2.45 gigahertz, and in Great Britain it is usually 0.896 gigahertz. Such a frequency can be in the range from 0.3 to 50 gigahertz (or higher) and is preferably in the range of 0.8 to 3 gigahertz. The readouts of the described apparatuses have as many as 40 characters in their alphanumeric displays and in some instances may include audible tones for operator feedback. The operator controls include a keyboard of up to 20 keys for input.

One of the advantages of the present invention is that the described microwave apparatus may be employed for ashing or in other operations for which each such apparatus may have been primarily designed, such as moisture determinations, volatiles analyses and for the promotion of chemical reactions. Usually when the apparatuses are employed for ashings of materials they will be used at their highest power supply condition, which is often about 560 to 1,000 watts. Times of ashing may be adjusted, as desired, and usually ashing times will be from 2 to 20 minutes or 5 to 15 minutes, but the furnace may be pre-heated over periods from 5 minutes to 2 hours, usually 20 to 60 minutes.

The main material of construction of the furnace, which is inserted into the previously described microwave system and is a part of the present apparatus, is one which is heat resistant, of low thermal conductivity and transmissive of microwave radiation. It has been found that such materials include ceramic, glass and quartz foams, with the quartz foams being highly preferred because they allow operations at higher temperatures, are of low thermal conductivities and are exceptionally transmissive of microwave radiation, being essentially or completely transparent to such radiation. Thus, it is considered that over 99% of the microwave radiation passes through the walls of the present furnaces unless it is absorbed by the microwave absorptive heating means in the furnace. Of the quartz foams those which are open celled and fused are even more preferable. Such materials are available from Emerson and Cuming, of Canton, Mass. and are marketed under the registered trademark ECCOFOAM Q. Two forms of ECCOFOAM ® Q are sold, ECCOFOAM Q-G and ECCOFOAM Q-R. The latter is heavier and stronger but for the purposes of the present invention it is preferred to employ the former. The characteristics of such fused quartz open celled foams are described in Technical Bulletin 6-2-12A, issued by such company, which bulletin is hereby incorporated herein by reference. It is considered that fused foam materials of the types mentioned are useful in making the present furnaces if they are of a density in the range of 0.3 to 0.8 g./c. cm., a modulus of rupture in the range of 10 to 50 kg./cm.$^2$, and a thermal conductivity in the range of 0.5 to 1.5 BTU/hr./sq. ft./°F./in. Such materials should also be operative in the ashing applications of the present invention at suitable ashing temperatures, which more preferably are in the range of 800° to 1,000° C. The foam quartz, which is essentially pure silicon dioxide, or foam ceramic should not decompose or deteriorate appreciably on subjection to such temperatures. When higher temperature ashings are to be undertaken an appropriate higher temperature material of construction will be employed, and the mentioned Eccofoams are preferred because they are stable at 1,650° C. for relatively short periods of time and are considered to be more stable at 1,090° C., to which they may be exposed for prolonged periods without adverse effects. The mentioned Eccofoam products are available from Emerson and Cuming in sheet form, said sheets measuring 30.5×45.7×7.6 cm. for the Eccofoam Q-G and 30.5×45.7×11.4 cm. for Eccofoam Q-R. Such sheets or slabs are machined to desired shape, utilizing abrasive cutting and grinding techniques. Although Eccofoam can be cemented to itself and other materials such cementing will almost always be avoided in making the present furnaces because the cements are usually ineffective at higher temperatures or are degraded at such temperatures.

The ashing means is of a microwave absorptive material which does not have a Curie temperature below desired ashing temperatures and which is capable of being heated by microwave radiation to a temperature in the range of 400° or 500° C. to 1,650° or 1,700° C. Sometimes the ashing range can be even higher, being limited by the melting, sublimation or decomposition points of the equipment materials being employed or of the ashable substance or its oxide(s), but normally the range of 600° to 1,000° C. is adequate and 800° to 950°, 975° or 1,000° C. is often more preferred. The ashing means is one which is stable at the intended use temperatures and is essentially or completely non-oxidizable at such a temperature. It should also be structurally sound at such use temperature, being resistant to disintegration, cracking and powdering. Although various materials are capable of absorbing microwave radiation and of being heated to temperatures in the ranges described, silicon carbide is the most useful and most preferred of such materials. Silicon carbide in powder, granular or other small particulate form (wherein the effective diameters of the particles are usually up to 0.5 to 1 cm.) can be heated by microwave radiation but generally in such a form it is not sufficiently effective to be employed as an ashing means for a variety of ashable materials such as may be encountered and for the analyses of which the present apparatus is intended. However, silicon carbide which is in continuous sintered or non-particulate solid form is very satisfactory and has been employed successfully in analyses of various materials for ash contents.

The continuous silicon carbide solid ashing means may be in various shapes or forms to suitably fit in a furnace wall cavity, but regular parallelepipeds are preferred, such as flat prisms of rectangular cross-sections. Suitable materials may be commercial "finishing sticks", which may be used to true grinding wheels; of these those sold by Norton Co. under the trademark CRYSTOLON, especially their Grade 37 C 220, which is a vitrified, bonded silicon carbide, are preferred, but other silicon carbide products may also be employed. Among these are Norton Co's. JKV finishing sticks and silicon nitride bonded silicon carbides, designated CN 137 and CN 233. Even if such products may physically deteriorate after many uses they are relatively inexpensive, so scheduled periodic replacements, such as after about every 1,000 analyses, may be undertaken but so far applicants have never had to replace any Crystolon silicon carbide. Other microwave absorptive heating elements that may be used include ferrites, garnets and similar materials known in the art.

The thermocouple that is employed to measure the temperature in the furnace during microwave heating thereof may be any such suitable thermocouple which is capable of withstanding the ashing temperature and is unaffected by any combustion products and any other gases released from the ashable material during ashing thereof. It has been found that a Type K thermocouple (chromel-alumel) is satisfactory in the invented apparatuses. In use such thermocouple includes a solid sheath which is electrically grounded to the chamber wall. It has been found in practice that the thermocouple operation and accuracy are not adversely affected by the microwave radiation. Instead of a thermocouple other temperature sensor devices can be used (with the temperature controls) to turn the magnetron power on and off, and thereby regulate the furnace temperature. Such may be infrared sensors, vapor pressure sensitive switches, bimetallic switches and expansion sensitive gauges, which all may be appropriately located in the apparatus and connected to a responsive temperature controller which can translate any signal received into on-off impulses or instructions to the magnetron switch.

The temperature controller is an electronic instrument of conventional design which opens and closes a magnetron electrical supply line in response to electrical signals from the thermocouple. It will be discussed further when the programming thereof is subsequently described. However other forms of the controller may be utilized with other temperature sensing devices.

The ashable sample should not be placed directly on the heating elements or microwave transmissive wall material of the furnace, as is evident, and therefore a support for the sample is employed. Such support should desirably be light in weight and must resist the high temperature of ashing. Also, it should be microwave transmissive, preferably microwave transparent or essentially microwave transparent (usually transmitting over 95% and preferably over 99% of such radiation), and it should not allow passage through it of the ashable sample or the resulting ash. A suitable support or container material for the ashable sample is a quartz microfiber (micron-sized) light weight filter material. Such material is desirably porous to facilitate air flow through it and yet does not allow passage therethrough of the microwave sample or ash. Normally the thickness of such filter material will be in the range of 0.2 to 0.7 mm. and the weight will be in the range of 50 to 150 g./m.$^2$. The particle retention efficiency of such material is about 99.999% for micron size particles and it is essentially free of various metals which could interfere with ash analyses (however a small percentage, e.g., 5%, of the filter may be of borosilicate glass microfibers). Such filter material may be employed in flat sheet form .s a support, with or without a cover sheet, or it may be in the form of a walled container, which walled form is considered to be preferable. Such quartz filters are described in Technical Data Sheet No. 860 QM-AA issued by Whatman Laboratory Products Inc., Clifton, N.J., which is incorporated herein by reference. A relatively minor disadvantage of the quartz filter material mentioned is that it apparently crystallizes and becomes brittle when subjected to elevated temperatures, such as those over about 500° C., for relatively long times. Nevertheless, it may be employed to hold the ashable sample and can be used repeatedly if care is taken. It is estimated that between five and fifty analyses can be run before a new container of quartz filter material should be put in service. Such items are relatively inexpensive and accordingly this "disadvantage" is not considered to be significant.

Other containers of non-porous materials may be employed to hold ashable samples during ashings, such as crucibles made of quartz, borosilicate glass, ceramic, porcelain and platinum but uses of these are normally limited to certain fusions and "dry ashings". For reasons which will be mentioned later, such containers are not as useful in normal microwave ashings as are supports and containers made of the described quartz microfiber filter material.

Virtually all materials that can be ashed within the operating temperature range for the present apparatus can be satisfactorily ashed in it. Among such materials there may be mentioned synthetic organic polymers, waste water sludges, activated sludges, industrial wastes, river, lake and stream bottom sediments, coals, foods, papers and building materials. Often the ash contents of such materials are as low as less than 1% or 0.1%, but they can be higher, even 10% and more, and the invented apparatus will reproducibly and accurately ash such diverse materials and retain all the ash in the described porous containers.

To set up the illustrated and described apparatus and to operate it the following procedure should be followed:

1. If the thermocouple is not in place it should be inserted into the microwave retaining chamber, as illustrated in FIGS. 1, 2, 4 and 5, and as previously described in the specification. The solid thermocouple sheath should be properly grounded to the chamber wall or other grounding location to prevent possible damage to the temperature controller.

2. Place the screen (73) and refractory block support (71) on the floor of the chamber.

3. Remove the top portion (57) of the ashing furnace and place it in the chamber under the thermocouple.

4. Align the hole in the top portion of the furnace with the thermocouple and raise such top portion upward so that the thermocouple is in the furnace cavity (23), which will be created by installation of the furnace bottom section (59).

5. While holding up the top portion of the furnace slide the bottom portion into the chamber and align it with the top portion.

6. Lower the top portion of the furnace onto the bottom portion. The thermocouple should extend into the ashing furnace cavity approximately 1 cm. but such distance may be adjusted as desired, based on evaluations of analytical results, and may be within 0.8 to 5 cm. from the top of the furnace cavity, preferably 0.8 to 3 cm. for the described furnace.

7. Place the door (35) in closed position on the ashing furnace.

8. Install the temperature controller on top of the microwave retaining chamber and insert the thermocouple plug into the back of the controller, and connect the temperature controller cable to the microwave system, as illustrated in FIG. 5.

9. Insert the microwave system and controller power cord plugs (not illustrated) into suitable electrical outlets and turn the controller power switch to ON position.

10. To minimize times required to heat the ashable samples, pre-heat the ashing furnace from room temperature to the desired ashing temperature, which desired ashing temperature is set into the temperature controller as described separately below. Then, program the microwave system for 60 minutes of microwave heating and set the power at 100%. Depress the START key and allow the furnace to pre-heat. The furnace will usually achieve an operating temperature of about 950° C. within 30 minutes or one of about 1,200° C. within an hour. If it is desired to hold the furnace temperature longer than 60 minutes the microwave system controls may be programmed for such longer time. Also, the ashing furnace temperature may re-programmed according to the controller programming procedure to be described below.

11. Place the amount of sample to be ashed in the container, or if several samples are to be ashed at the same time, place them in a plurality of containers.

12. Depress the STOP key, open the chamber door, remove the furnace door and place container(s) of ashable sample(s) in the ashing furnace cavity, using tongs. Replace the furnace door, closing it or leaving it slightly ajar, if preferred, and then close the chamber door.

13. Push the RESET button and depress the START key, which turns on the magnetron and starts heating of the sample(s).

14. After completion of ashing, which usually takes about 10 minutes at the desired temperature, depress the STOP key, open the chamber door and remove the furnace door (which can easily be done by hand despite the high internal temperature of the furnace). Employ tongs to remove the container(s) of ash and allow it/-them to cool to room temperature. Replace the furnace door after removal of the container(s) to prevent heat damage to the chamber door. Then close the chamber door and depress the START key, to maintain the furnace at ashing temperature.

The following is a description of the procedure to be employed to program the temperature controller.

1. Insert the thermocouple plug into the controller. the S key on the controller and 0 will appear on the controller display. Press the Increase key and hold it until 28 appears on the display. If 28 is overshot, press the Decrease key until 28 is reached.

2. Press the S key and °C. or °F. will appear.
  a. If °C. appears and °C. is the desired readout, proceed to step 3.
  b. If °C. appears and °F. is the desired read-out, press the Decrease key and °F. will appear, and then proceed to step 3.
  c. If °F. appears and °F. is the desired read-out, proceed to step 3.
  d. If °F. appears and °C. is the desired read-out, press the Increase key and °C. will appear, after which proceed to step 3

3. Press the S key and SP1H will appear momentarily. Press the Increase or Decrease key until the desired operating temperature set point appears. This sets the upper temperature limit, SP1H. The maximum operating temperature is designed into the controller circuitry. For example, it may be 1,200° C. in some instances or 1,650° C. in others, depending on the construction of the apparatus.

4. Press the S key and SP1L will appear momentarily. Then press the Increase or Decrease key unit 0 appear. This sets the lower temperature limit SP1L.

5. Press the S key and SP2H will appear momentarily. Then press the Increase key unit 2499, the maximum value, appears. This sets the upper limit value SP2H, which is not used in the program but is needed to make the unit operate properly.

6. Press the S key and SP2L will appear momentarily. Then press the Increase or Decrease key until 0 appears. This sets the lower limit value, SP2L, that also is not used in the program but is needed to make the unit operate properly.

7. Press the S key and HYS will appear momentarily. Then press the Increase or Decrease key until 1 appears. This sets the operating deadband for maximum operation precision.

8. Finally, press the S key and RUN will appear momentarily. The actual temperature of the ashing furnace will then appear. Controller programming is now complete. Such programming must be completed within two minutes or the controller will exit the programming mode and it will be necessary to perform steps 1–8 again.

It will be noted that by following the immediately foregoing instructions (steps 1–8) for controller programming, upper and lower temperature limits are set into the controller program. Such set points may be identical, in which case when the measured temperature falls below a predetermined hysteresis value (which is usually 2 or 3 degrees) the magnetron will be turned on again, and it will be turned off when the measured temperature increases to about the same value above the set temperature. Thus, the temperature in the furnace cavity is controllable to within 5° C. or 10° C. of a set ashing temperature by the thermocouple and controlling means.

The ashing apparatus of this invention is controlled by a combination of temperature controller and single chip type microprocessor. The microprocessor executes instructions from permanent storage in an internal EPROM. In operation the microprocessor receives commands and time data from an operator through the microwave instrument or system keyboard. The operator may view a response to most of the commands on the accompanying 20 digit alphanumeric display.

When the operator enters the time data on the keyboard, the data is stored in temporary RAM memory. Once time has been entered for Stage 1 the microprocessor will allow entry of a Start command. When Start is pressed the microprocessor changes one of its output lines from high to low and begins to count down the time. This digital low is wired through a set of normally closed contacts in the temperature controller and then to the microwave solid state relay (SSR). This low turns on the SSR, which controls microwave power. The SSR, in turn, then switches on the alternating current (AC) to the microwave high voltage section and the magnetron generates microwave energy.

Microwave energy directed into the furnace cavity heats up the ashing furnace heating elements, which heat the furnace cavity and the sample to be ashed. The thermocouple senses the temperature of the ashing furnace and the output of the thermocouple is communicated to the temperature controller, which continually compares the measured temperature to the set point temperature, which has previously been entered. When the measured temperature equals the set point temperature the temperature controller opens the normally closed contact and interrupts the digital signal that had previously turned on the SSR. Without this signal the microwave energy ceases and the ashing furnace holds at this set point temperature and slowly begins to cool. When the measured temperature falls below a predetermined hysteresis value (usually 2 to 3 degrees), the controller closes the opened contact and the SSR is turned on. The microwave energy then raises the temperature of the ashing furnace to the set point temperature. Such processes continue until the total heating time, as set by the operator, has counted down to 0. The microprocessor changes the digital signal back to a high state and microwave heating and control cease. At any time during the countdown the operator may press the Stop key to stop the countdown and to halt the heating process, if that should be desired.

In the above description the temperature controller is separate from the microwave instrument (CEM Microwave Drying/Digestion System MDS-81) because the MDS-81 system was available "hardware" which could be used in conjunction with a less complex new controller. However, it is within the invention to integrate the temperature controller into the microwave instrument.

To ash an ashable sample in the present apparatus is a simple procedure. All that is required is to place the sample in a suitable container, of the type previously described, and insert it into the furnace cavity, close the furnace door and the chamber door, and press the Start button. After ashing temperature has been reached most samples will be completely ashed within about ten minutes but completion of ashing can be verified by weighing the ashed sample (in the container, after cooling) and re-weighing after additional exposure to the ashing conditions. When the weight ceases to decrease completion of ashing is established, and so is the time needed to effect complete ashings, although one will usually employ additional time, say a 20% excess, to be sure. In such weighings the ashed sample and container should not be weighed hot but should be conditioned for weighing, as is known in the art, but such conditionings proceed very quickly with the invented support.

Normally the present apparatus and process are employed in analyzing materials for ash content. In such procedures the container is weighed without and with ashable sample content before ashing, and the container, with ash, is weighed after complete ashing. The percentage of ash in the original sample can then be readily calculated by dividing the ash weight by the sample weight and multiplying by 100. However, in some ashing operations it is common to employ a dispersing agent, such as magnesium acetate, which acts to prevent production of a vitreous or glass-like residue in the ashing container, which residue may contain some unashed sample. Without the use of such a dispersing agent false high or low readings for ash content could be obtained. When the dispersing agent is employed a blank run will normally be made to determine how much of the apparent ash weight is actually ashed dispersing agent, and such weight will be subtracted from the apparent ash weight to give the true ash weight.

Although various weights of samples and various numbers of containers of ashable samples may be employed in the ashing apparatuses of this invention, in a typical such apparatus, in which the furnace cavity is approximately 14 cm. × 14 cm. or about 200 sq. cm. in area, one will normally charge up to 4 or 5 porous, heat resistant and microwave transmissive containers of ashable sample, which containers will preferably be in short cylindrical form of base area of about 15 to 25 sq. cm. each, e.g., about 20 sq. cm., and with heights in the range of 0.8 to 2 cm., e.g., about 1 or 1.5 cm. Desirably, the weight of such containers will be as low as possible, usually being in the range of 0.2 to 1 g. each, preferably 0.3 to 0.6 g., e.g., about 0.4 or 0.5 g. The weight of ashable sample will normally be in the range of 1 to 10 g., preferably being in the range of 1.5 to 6 g., e.g., about 2 or 5 g. Ash contents may be high or low, up to a maximum of about 50% and to a minimum of 0.001% or even less. For materials like unfilled synthetic polymeric plastics and grain flours, such will usually be comparatively low, normally being less than 5% and frequently being less than 1%, such as from 0.01 to 0.8%. For the charges of ashable material mentioned, with ash contents in the ranges recited, magnesium acetate dispersing agent is normally employed, dissolved in ethanol (95%), so that the ethanol solution is of a magnesium acetate concentration of about 15 g./l. About 3 ml. of the solution are dripped onto the ashable sample while it is in the container and, if the container employed is porous and of light weight heat resistant and microwave transmissive quartz micro-fibers, the solution will wet the entire ashable sample and will also wet the fibers of the container because of container porosity, microfibrous quartz nature, and container design, and the alcohol flashes off during heating in a "gentle" manner, not carrying ash or sample out of the container, whereas when impermeable or conventional containers are employed, such as platinum crucibles, vaporization and combustion of the alcohol are often more violent and sometimes quantities of samples are carried out of the container, leading to false ash determinations.

The ashing temperature, as it is set for the furnace cavity, is normally in the range of 400° to 1,600° C. but such temperature should be chosen in light of the characteristics of the ashable sample and the microwave ashing apparatus. Many ashings and analyses are conductable below 1,200° C. and a large number are conductable in the range of 600° to 1,000° C., such as 950° C. Thus, ashings of wheat and other grain flours may be effected at about 870° or 950° C. and ashings of polyethylene and polypropylene may take place at about 550° C. Ashing times may be adjusted accordingly, but will normally be in the range of 5 to 20 minutes, preferably 8 to 15 minutes, e.g., about 10 minutes. In some instances the ashing apparatus will be programmable so that the furnace temperature will be changed during the run. In such a situation sometimes the first heating or ramp temperature may be comparatively low, e.g., about 100° C., to dry the sample, after which it may be increased to full ashing temperature.

The present invention possesses many significant advantages over prior art apparatuses and processes for ashing materials and for analyzing such materials for ash contents. It is automatic and allows a single operator to run a multiplicity of ashing operations and analyses in a plurality of ashing apparatuses, each of which may contain a plurality of ashing specimens. The controllable heating of the ashable sample is very uniform, with little heat being lost from the furnace cavity, because the walls thereof are of very low thermal conductivity (and they are also resistant to chemical reactions with combustion products and decomposition products of the ashed material). As was previously referred to, when the container for the ashable sample is of a porous sheet of quartz microfibers the removal of ethanol (and the accompanying small proportion of water) from the sample that has been treated with dispersing agent may be effected without the need for external ignition of the ethanol and without the loss of sample in any "explosion" such as may occur when conventional crucibles are employed, as in conventional muffle furnaces. The analyses, in addition to being undertaken under more controllable conditions, are also appreciably faster than conventional muffle furnace analyses and the results are just as accurate (actually it is considered that they are more accurate).

The apparatus is easy to set up and easy to use. It is not necessary to wait long times for parts to cool down so that they can be handled by an operator. For example, the furnace door may be removed from the furnace by hand immediately after completion of an ashing operation because, despite the high internal temperature of the furnace, the door and the exterior walls thereof are not hot enough to burn the fingers of an operator touching them. Such is attributable to the low thermal conductivity of the material of construction of such door and the furnace walls, and to the continuous cooling of such surfaces by the air circulating in the microwave retaining chamber.

Air flow into the furnace is also controllable and contributes to the quicker ashing that has been obtained. The portion of the air that is drawn into the chamber passes through the furnace, in part due to a chimney effect. Thus, gases that are generated during ashing of a sample rise up and exit the furnace through upper portions thereof, drawing replacement air into the furnace through lower portions thereof. The venting passageway in the top of the furnace (through which the thermocouple probe passes)carries combustion gases out of the furnace past the thermocouple, keeping the thermocouple sensor sections in contact with circulating gas rather than with stagnant gas, so that the temperature at the sensor corresponds to the actual furnace temperature (and the temperature being applied to the ashable sample). The flow rate of air through the furnace can be employed to regulate the rate of ashing of the ashable sample. Such rate is readily adjusted by cracking open the furnace door, which can be effected, even during high temperature heating of the furnace, by hand operation, involving finger contact with the door handle or gripping means. Fan or blower speed can also be changed to change air flow rates through the furnace but such is unnecessary because the furnace door opening gives good control.

The light weight and low mass microfiber quartz ashing containers utilized are porous and therefore they allow air to flow through the walls thereof and into contact with the ashable sample, thereby accelerating the ashing process. Because such containers are light in weight they tend to cool very quickly after being removed from the furnace cavity, typically taking only 10 to 90 seconds, e.g., 60 seconds, to cool, which cooling is desirably in a desiccator. Such cooling time is much less than that which is normally required when other containers, such as platinum or porcelain crucibles, are used.

It may be considered that in the present apparatus the "microwave system", including chamber, blower, ductwork and associated parts, acts as a fume hood for the contained microwave furnace, and does that without the usual space requirement for such a fume hood, without the undesirable heating of the laboratory due to the use of a muffle furnace, and without danger to operating personnel of burning by contacts with heated parts.

The following examples illustrate, but do not limit the invention. Unless otherwise indicated, all parts are by weight and all temperatures are in °C.

EXAMPLE 1

An official sample of wheat flour was analyzed for ash, utilizing the microwave ashing apparatus of this invention, as described in the previous specification, and the results obtained were compared to those that had resulted from standard analyses in which muffle furnace heating had been employed. Ten "experimental" runs were made, using either single containers of test sample or a plurality of such containers in the ashing apparatus at a time. The wheat flour employed was the standard, which was a check sample obtained from the American Association of Cereal Chemists. The ashing apparatus employed was a 1,000 watt CEM Corporation MDS-81 Microwave Drying/Digestion System unit, modified as described in the specification and employed in conjunction with a thermocouple, a temperature controller and a furnace of the types described previously herein. The materials of construction of the furnace were ECCOFOAM Q-G for the furnace body and door, and Norton Co. Crystallon Grade 37C220 silicon carbide for the heating elements. The base area of the furnace is about 200 sq. cm., with the furnace cavity measuring about 14 cm. ×14 cm. in horizontal cross-section, and being about 5 cm. high. The thermocouple is of chromel-alumel type and the circuitry is that of FIG. 6.

The microwave ashing apparatus is set for a temperature of 950° C. and is pre-heated to such temperature for about ½ hour. Then the chamber door and the furnace door are opened and a walled container of the sample is inserted into the furnace, using tongs. The container is made of quartz microfiber filter sheet designated QM-A by the manufacturer, Whatman Laboratory Products Inc., and is in the shape of a flat cylinder 5 cm. in diameter with a wall height of about 1.5 cm. It contains 2.1241 g. of wheat flour sample and about 3 cc. of a 15 g./l. solution of magnesium acetate in ethanol (95%), which had been dripped onto the sample so as to wet all of it, and the adjacent container bottom and wall. After insertion of the container of sample the furnace door is replaced, in such position that a passageway about 0.3 cm. wide is left, between the door and the furnace wall. Shortly after addition of the container and test sample to the furnace the alcohol burns off without incident. Ten minutes after charging of the furnace with the sample, the doors are opened and the container is removed, using tongs, and is allowed to cool in a desiccator, which takes about 60 seconds. The container, with the ash and magnesium oxide residue (from the magnesium acetate) therein, is then weighed. Previously, the container had been weighed empty and the equivalent magnesium oxide residue had been determined for the amount of magnesium acetate solution employed. The amount of ash was 0.0112 g. and the sample weight was 2.1241 g., so the percentage of ash in the sample was 0.527%.

The above ashing determination was repeated nine times, for a total of ten such determinations. Results for these runs are given in Table 1, below.

TABLE 1

| Run Code | A | B | C | D | E | F | G | H | I | J |
|---|---|---|---|---|---|---|---|---|---|---|
| Wt. of Container + Ash + MgO (g.) | 0.5015 | 0.5014 | 0.5228 | 0.5890 | 0.4878 | 0.4940 | 0.5173 | 0.5060 | 0.5790 | 0.4753 |
| Wt. of Container (g.) | 0.4893 | 0.4808 | 0.5024 | 0.5668 | 0.5656 | 0.4732 | 0.4967 | 0.4856 | 0.5567 | 0.4528 |
| Wt. of Ash + MgO (g.) | 0.0212 | 0.0206 | 0.0204 | 0.0222 | 0.0222 | 0.0208 | 0.0206 | 0.0204 | 0.0223 | 0.0225 |
| Wt. of MgO (g.) | 0.0100 | 0.0100 | 0.0100 | 0.0115 | 0.0115 | 0.0100 | 0.0100 | 0.0100 | 0.0115 | 0.0115 |
| Wt. of Ash (g.) | 0.0112 | 0.0106 | 0.0104 | 0.0107 | 0.0107 | 0.0108 | 0.0106 | 0.0104 | 0.0108 | 0.0110 |
| Wt. of Sample (g.) | 2.1241 | 2.0392 | 2.0142 | 2.0144 | 2.0305 | 2.0659 | 2.0378 | 2.0276 | 2.0529 | 2.0426 |
| Ash Content (%, by weight) | 0.527 | 0.520 | 0.516 | 0.531 | 0.527 | 0.523 | 0.520 | 0.513 | 0.526 | 0.539 |

As is seen from Table 1, the high determination is 0.539% and the low determination is 0.513%. The average is 0.524%. According to the American Association of Cereal Chemists, fifty-one analyses by muffle furnace ashing techniques, using an oven temperature of 871° C. for one hour, yielded a high of 0.550% and a low of 0.504%, with an average of 0.530%. Thus, it appears that the microwave ashing apparatus yielded more consistent results and has been proven to be sufficiently accurate to be employed in replacement of the muffle furnace ashing procedure.

EXAMPLE 2

Two additional wheat flour samples, identified as B and C, were subjected to microwave ashing and ash contents of these samples were determined and compared to results obtained by standard muffle furnace analyses. The procedures followed were the same as those of Example 1. For sample B three test runs were made and the ash content results were 0.508%, 0.512%, and 0.520%, giving an average of 0.513%. The ash content by standard muffle furnace analysis was 0.512%.

In three microwave ash analyses of Sample C the results were 0.724%, 0.724% and 0.739%, giving an average of 0.729%. The standard analysis of the same sample resulted in a finding of an ash content of 0.730%.

EXAMPLE 3

A sample of polyethylene was analyzed for ash, using the apparatus and method described in Example 1 but omitting the magnesium acetate. Three samples of the same polyethylene were tested, with the ashing temperature being held at 550° C.±3° C. for ten minute periods. Ash contents of 0.008%, 0.008% and 0.006% were obtained, with the average being 0.007%. The various weighings for the three runs made are given in TABLE 2, as are the ash contents.

TABLE 2

| Run Code | Q | R | S |
| --- | --- | --- | --- |
| Wt. of Container + Ash (g.) | 0.6032 | 0.5972 | 0.5874 |
| Wt of Container (g.) | 0.6028 | 0.5968 | 0.5869 |
| Wt. of Ash (g.) | 0.0004 | 0.0004 | 0.0005 |
| Wt. of Sample (g.) | 5.0187 | 5.0082 | 8.0695 |
| Ash Content (%, by weight) | 0.008 | 0.008 | 0.006 |

In a manner described for the ash analysis of polyethylene three samples of polypropylene material were analyzed for ash content, using the apparatus and process of this invention. Ash contents determined were 0.024%, 0.025%, 0.024%, with the average being 0.024%. The various weighings are reported in TABLE 3, as are the ash contents.

TABLE 3

| Run Code | I | U | Y |
| --- | --- | --- | --- |
| Wt. of Container + Ash (g.) | 0.5984 | 0.5939 | 0.5903 |
| Wt. of Container (g.) | 0.5972 | 0.5926 | 0.5884 |
| Wt. of Ash (g.) | 0.0012 | 0.0013 | 0.0019 |
| Wt. of Sample (g.) | 5.0103 | 5.1606 | 8.0431 |
| Ash Content (%, by weight) | 0.024 | 0.025 | 0.025 |

EXAMPLE 4

The described microwave ashing apparatuses and processes are useful for performing microwave ash analyses of various other materials, including other foods and other synthetic organic polymers, various sludges and waterway sediments, papers, coals and building materials. The ash contents found in analyses of such materials often range from less than 0.1% to 10% or more and such analyses are readily performed and yield accurate results, compared to standard muffle furnace analyses. Of course, ashing times are substantially reduced, compared to muffle furnace ashing times. Other ashing temperatures are employable, ranging from 400° to 1,200° C., and temperatures as high as 1,600° C. are feasible, with ashing times ranging from 5 to 20 minutes. To ash materials at such highest temperature some modifications of the apparatus and the microwave instrument may be desirable.

In carrying out these additional analyses the apparatus size may be changed, the wattage may be modified and the ashing procedures may be altered. Thus, in some cases a 600 watt or 900 watt basic unit (CEM MDS-81) is employed or such basic unit is replaced by other suitable microwave instrument of such general type, modified as required. Instead of employing the porous quartz microfiber container to hold the sample being ashed one may use a porcelain or quartz container or one made of other suitable material. In such cases the ashing procedure may be varied by ignition of the alcohol accompanying the magnesium acetate (when such is employed) external to the furnace (to avoid loss of sample due to sometimes violent ignitions in the furnace). Sometimes, even when the porous quartz microfiber container is used, if any alcohol present is not removed first by evaporation by low temperature heating, it may be considered desirable to remove the furnace door during the initial heating of the sample so that the flaming of the alcohol can be more controlled and so any loss of sample can be prevented.

As was previously mentioned, air flow rates through the furnace may be adjusted by opening or closing the furnace door. Such flow rates depend on the degree of such opening and also depend on the total air flow rate through the chamber, which will usually be in the range of 1 to 5 cu. m./min. The total air flow and the various openings into and out of the furnace, in combination, will continue to supply air to the vicinity of the material being ashed so that as the products of combustion are removed they are replaced with fresh air. Despite the relatively large air flow through the chamber the ashing temperature is maintainable within the furnace because of the good insulating properties of the furnace wall and door and because of the relatively minor proportion of gas that enters and leaves the furnace during ashing, with most of the air passing around the furnace.

Other variations of apparatus and process include employing other radiation absorptive materials instead of silicon carbide, e.g., ferrites, installing a quartz fiber safety screen over the ashing container, employing a radiation transparent turntable to provide even more uniform heating of the ashable sample, and varying the size and shape of the furnace to improve even heating and control of air flow through it. Although a turntable would promote more even heating of the microwave absorbent heating elements it has been found that furnace temperatures are essentially uniform throughout and multiple ashable samples are evenly ashed. This is attributable to the excellent insulating properties of the quartz foam (Eccofoam) furnace material. Accordingly, turntables and special radiation mixers are not needed.

The invention has been described with respect to various working examples, embodiments and illustrations thereof but is not to be limited to these because it is evident that one of skill in the art, with the present specification before him/her, will be able to utilize substitutes and equivalents without departing from the invention.

What is claimed is:

1. An apparatus for ashing ashable materials which comprises: a walled microwave retaining chamber; a source of microwave radiation for radiating onto contents of said chamber, which contents include said ashable material; an ashing furnace within said chamber having a furnace wall of heat resistance material about an internal furnace cavity, with an opening in said furnace wall for insertion and removal of said ashable material, a door of heat resistant material for closing and opening said opening in said furnace wall, a microwave absorptive material which has a surface thereof exposed to said furnace cavity, which microwave absorptive material is capable of being heated to an ashing temperature by microwave radiation, and a passageway through said furnace for passing gas into the furnace cavity and for venting gas from said cavity, which passageway includes an upper portion through which gas is removed from an upper portion of the furnace cavity, with the furnace wall and furnace door being of heat resistant material of low thermal conductivity which is essentially transparent to microwave radiation; a temperature sensor; for sensing the temperature in the ashing furnace, which sensor is located in said upper portion of said passageway through the furnace and is of a size that allows passage of gas past it from the furnace cavity to the chamber through a clearance in the passageway; and controlling means, responsive to the temperature sensor, for controlling the source of microwave radiation and thereby controlling the temperature in the ashing furnace.

2. An apparatus according to claim 1 wherein the passageway through the furnace for passing gas into the furnace cavity and for venting gas from said cavity includes an opening between the furnace door and the furnace door opening, through which gas can enter the furnace.

3. An apparatus for ashing ashable materials which comprises: a walled microwave retaining chamber; a source of microwave radiation for radiating onto contents of said chamber; an ashing furnace within said chamber having a furnace wall of heat resistant material about an internal furnace cavity, with an opening in said furnace wall for insertion and removal of an ashable sample, a door of heat resistant material for closing and opening said opening in said furnace wall, a microwave absorptive material which has a surface thereof exposed to said furnace cavity, which material is capable of being heated to an ashing temperature by microwave radiation, and a passageway through said furnace for passing gas into the furnace cavity and for venting gas from aid cavity, with the furnace wall and furnace door being of heat resistant material of low thermal conductivity which is essentially transparent to microwave radiation; a temperature sensor, for sensing the temperature in the ashing furnace, which sensor is located in said passageway through the furnace and which is of a size to allow passage of gas from the furnace cavity to the chamber through a clearance in the passageway; controlling means, responsive to the temperature sensor, for controlling the source of microwave radiation other thereby regulating the temperature in the asking furnace; and inlet and outlet openings in the microwave retaining chamber wall for passage of gas into and out of said chamber, around said furnace.

4. An apparatus according to claim 3 wherein the door for the furnace wall is removable from the furnace wall to enable chargings of the furnace with containers of ashable samples and removals of such containers after ashings, when the furnace is still hot, which door has handle or gripping means on an exterior portion thereof, and is of a material of low thermal conductivity so that the handle can be grasped by the fingers of an operator while the interior of the door is at or near ashing temperature, without burning the operator.

5. An apparatus according to claim 3 wherein the wall and door of the ashing furnace are of an open cell ceramic foam which is transparent to microwave radiation and is of low thermal conductivity, the microwave absorptive material is silicon carbide, and the furnace door and wall opening are so shaped that the door may be partially opened to permit controlled air flow into the furnace through the passageway resulting.

6. An apparatus according to claim 3 wherein the source of microwave radiation is a magnetron and the temperature in the furnace cavity is controllable by the temperature sensor and controlling means, which turn the magnetron on when the temperature in the furnace cavity is less than a set temperature and which turn it off when the temperature in the cavity is more than such set temperature.

7. An apparatus according to claim 3 wherein the ashing furnace wall is of separable upper and lower portions and is of open cell ceramic foam and, with the furnace door, which is of open cell ceramic foam, defines said furnace cavity having a top, a bottom and sides, with the sides and bottom being at least partially lined with silicon carbide.

8. An apparatus according to claim 3 wherein there is present in the furnace cavity at least one heat resistant container for holding an ashable analytic sample.

9. An apparatus for ashing ashable samples which comprises: a walled microwave retaining chamber; a source of microwave radiation for radiating onto contents of said chamber; an ashing furnace within said chamber having a furnace wall about an internal furnace cavity, with an opening in said furnace wall for insertion therein and removal therefrom of an ashable sample, a door for closing and opening said opening in said furnace wall, a microwave absorptive material which has a surface thereof exposed to said furnace cavity, which absorptive material is capable of being heated to an ashing temperature by microwave radiation, a passageway through said furnace for passing gas into the furnace cavity and for venting gas from said cavity, said passageway comprising an opening in an upper portion of the heat resistant wall of the asking furnace for passage of gas from the furnace cavity to the chamber, with the furnace wall and furnace door being of heat resistant material of low thermal conductivity which is essentially transparent to microwave radiation; a thermocouple; a controlling means, responsive to said thermocouple, for controlling the source of microwave radiation and thereby regulating the temperature in the ashing furnace; and electrically conducting means for connecting the controlling means and the thermocouple; with the thermocouple being located in the opening in the upper portion of the wall of the ashing furnace and with said opening being larger than the thermocouple so as to allow passage of gas from the furnace cavity to the chamber through a clearance between said opening and said thermocouple; and inlet and outlet openings in the microwave retaining chamber wall for passage of gas into and out of said chamber, around said furnace.

10. An apparatus according to claim 9 wherein the walled microwave retaining chamber has a doorway opening therein and a door to selectively close and open the doorway, with such door and doorway being aligned with the furnace opening and door so that ready access to the furnace cavity is obtainable through the chamber opening and furnace opening when both the chamber door and the furnace door are in open positions.

11. An apparatus according to claim 10 wherein the ashing furnace wall is made of a quartz or ceramic foam which is stable at furnace cavity temperatures up to 1,000° C., the microwave absorptive material is silicon carbide, the source of microwave radiation is a magnetron, and the temperature in the furnace cavity is controllable within 10° C. of a set ashing temperature, up to 1,000° C., by the thermocouple and controlling means, which turn the magnetron on when the temperature in the cavity is less than the set temperature and which turn it off when the temperature in said cavity is more than the set temperature.

12. An apparatus according to claim 11 wherein the wall of the ashing furnace is made of an open celled fused quartz foam which is of a density in the range of 0.3 to 0.8 g./c. cm., the open celled fused quartz foam is stable at a furnace cavity temperature up to 1,650° C., and the temperature in the furnace cavity is controllable to within 5° C. of a set ashing temperature in the range of 600° to 1,000° C. by the thermocouple and controlling means.

13. An apparatus according to claim 12 wherein the ashing furnace wall that defines the furnace cavity and the furnace wall opening for the door is made of upper and lower unitary pieces of the open celled fused quartz foam and the furnace door is made of a separate piece of the same material.

14. An apparatus according to claim 13 wherein the ashing furnace wall defines said furnace cavity having top, bottom and side portions, with the sides and bottom being at least partially lined with silicon carbide, and the furnace door is substantially of trapezoidal shape in horizontal cross-section, and fits with said opening in the furnace wall, enabling removal of the door, partial opening, and closure thereof, as desired.

15. An apparatus according to claim 14 wherein the bottom portion of the ashing furnace includes grooves for insertion of silicon carbide strips or slabs therein, and the furnace door includes handle or gripping means to enable holding of said door with an operator's fingers when it is being opened or closed.

16. An apparatus according to claim 15 wherein there is present in the furnace cavity at least one heat resistant container for holding analytical sample(s).

17. An apparatus according to claim 16 wherein at least one said container for the analytical sample(s) is a light weight walled container of essentially microwave transparent quartz microfibers which allow gas flow therethrough but prevent passage of ash therethrough.

* * * * *